(12) United States Patent  
Larsson

(10) Patent No.: US 8,153,147 B2
(45) Date of Patent: Apr. 10, 2012

(54) HEPARIN COATING OF BIOLOGICAL TISSUE

(75) Inventor: Rolf Larsson, Uppsala (SE)

(73) Assignee: Corline Systems AB, Uppsala (SE)

( * ) Notice: Subject to any disclaimer, the term of this patent is extended or adjusted under 35 U.S.C. 154(b) by 919 days.

(21) Appl. No.: 11/994,457

(22) PCT Filed: Jun. 28, 2006

(86) PCT No.: PCT/SE2006/050224
§ 371 (c)(1),
(2), (4) Date: Jul. 7, 2008

(87) PCT Pub. No.: WO2007/004975
PCT Pub. Date: Jan. 11, 2007

(65) Prior Publication Data
US 2009/0098174 A1    Apr. 16, 2009

(30) Foreign Application Priority Data
Jul. 1, 2005    (SE) ...................................... 0501534

(51) Int. Cl.
*A61K 31/727*    (2006.01)
*A61K 35/12*     (2006.01)
*A61F 2/02*      (2006.01)

(52) U.S. Cl. ......... 424/422; 424/572; 424/93.7; 514/56; 435/7.5

(58) Field of Classification Search .................. 424/422, 424/572, 93.7; 435/7.5; 514/56
See application file for complete search history.

(56) References Cited

U.S. PATENT DOCUMENTS

| 5,773,224 A | 6/1998 | Grandics et al. | |
| 2001/0012538 A1 * | 8/2001 | Ung-Chhun et al. | 427/2.25 |
| 2001/0044654 A1 * | 11/2001 | Chen et al. | 623/1.41 |
| 2003/0129130 A1 | 7/2003 | Guire et al. | |

FOREIGN PATENT DOCUMENTS

| WO | 0040253 A1 | 7/2000 |
| WO | 0048537 A1 | 8/2000 |

OTHER PUBLICATIONS

Warren C. Kett, et al., "Avidin is a heparin-binding protein. Affinity, specificity and structural analysis", Biochimica et Biophysica Acta, 1620, 2003, pp. 225-234.

* cited by examiner

*Primary Examiner* — Taeyoon Kim
(74) *Attorney, Agent, or Firm* — Browdy and Neimark, PLLC

(57) ABSTRACT

The present invention discloses an in vitro method to provide biological tissue with a heparin coating comprising the following steps; linking a biotin reagent to biological tissue, linking an avidin reagent to the biotinylated biological tissue, and linking a heparin reagent to the formed layer of avidin on the biological tissue thus forming a heparin coating. The invention further discloses a heparin coating on biological tissue, the use of a heparin coating, and the biological tissue coated with a heparin layer according to the method.

14 Claims, 1 Drawing Sheet

Recording by QCM of the process of heparin coating on avidin

Fig 1. Recording by QCM of the process of heparin coating on avidin
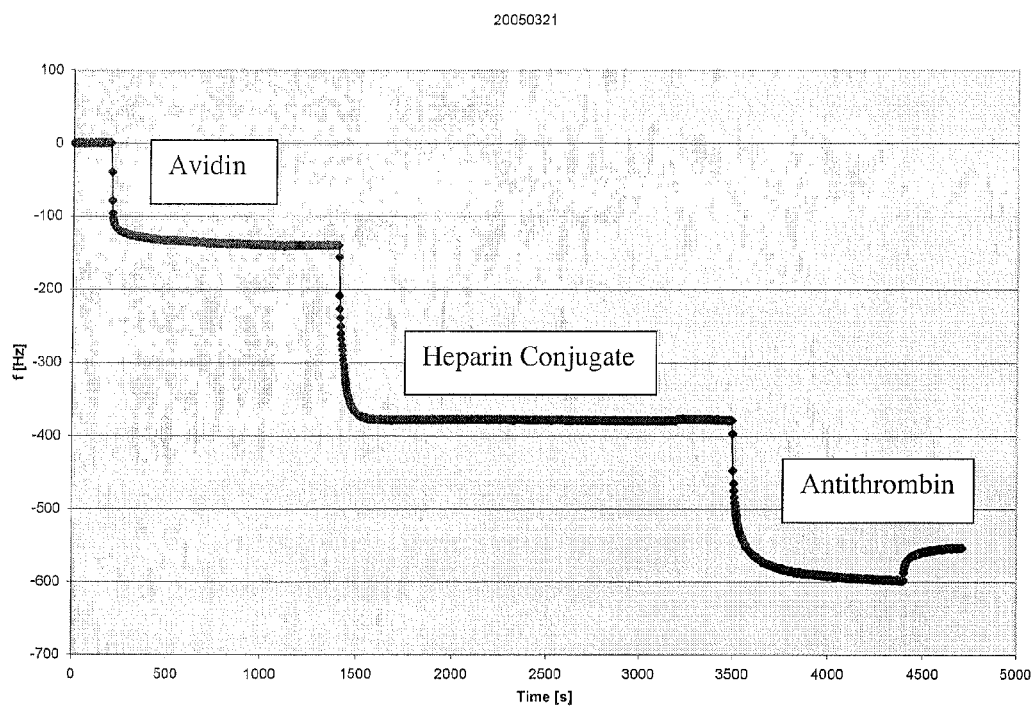
Fig 2. Picture obtained by confocal microscopy of a heparin coated islet.
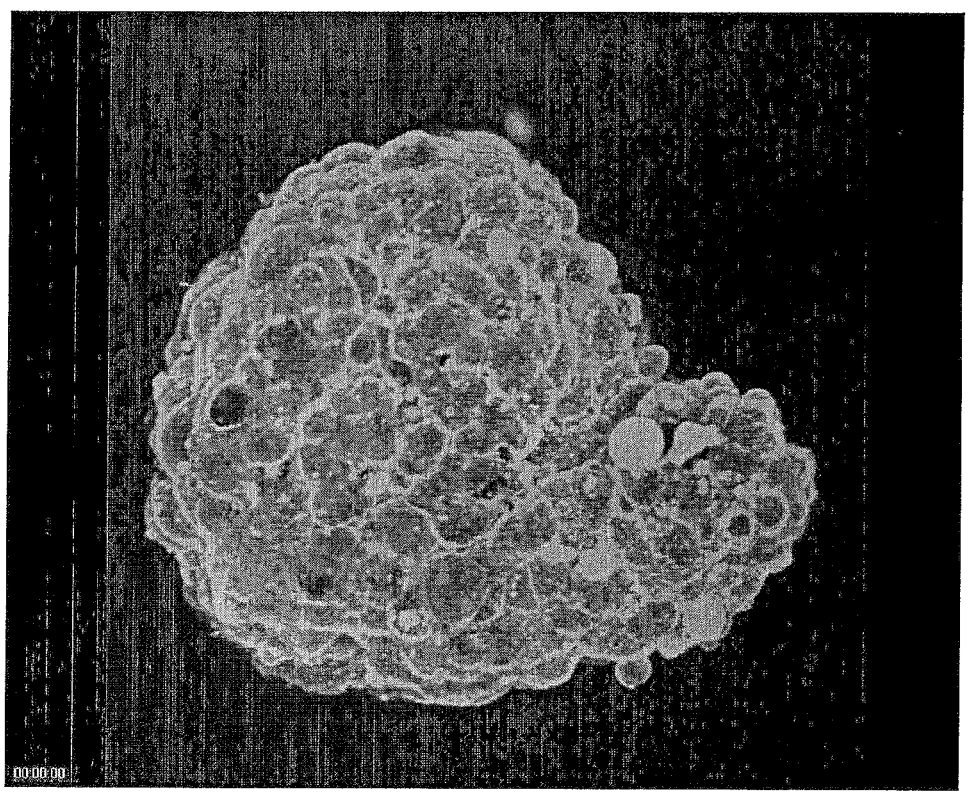

HEPARIN COATING OF BIOLOGICAL TISSUE

FIELD OF THE INVENTION

The present invention relates to an in vitro method for providing biological tissue with a heparin coating.

BACKGROUND OF THE INVENTION

The innate immune system of mammals is designed to distinguish between endogenous and exogenous structures. As soon as exogenous structures are exposed they will be recognised by the innate immune system and a number of defence systems are recruited and initiated, which may lead to accelerated activation of coagulation and inflammation. The blood vessels are covered by endothelial cells which express heparan sulphate (a heparin-like substance) at the outermost layer. Like heparin, heparan sulphate exhibits carbohydrate regions capable of accelerating the inhibitory effect of antithrombin. Due to pathological processes that may be initiated by e.g. lack of oxygen (ischemia), mechanical damage, etc., the chemical and biological constitution of the involved tissue may be changed so that the tissue will be recognised as exogenous. In the area of tissue engineering, isolation and processing of cells (as e.g. islets of Langerhans) may lead to exposure of exogenous structures when such cells are transfused to blood, consequently leading to loss of biological function, and even destruction, of the cells due to instant blood mediated inflammatory response (IBMIR), (Diabetes, vol. 48, 1907-1914, 1999)

PRIOR ART

The patent application PCT/SE00/00223 discloses a way of providing islets of Langerhans with a surface coating of a heparin conjugate by a one-step procedure basically relying on an ionic interaction between the negatively charged heparin conjugate and positive charges at the islet surface. Although a one-step procedure is attractive, recent evaluations have indicated that it may be difficult to obtain reproducible results with this relatively simple approach possibly due to the fact that the surface characteristics of isolated islets may vary from one preparation to the other. Hence, a procedure with an improved reproducibility and of such nature that it can be applied to a wide variety of biological tissues would be highly desirable.

The patent application WO 03/000234 discloses an open porous matrix for medical use in or on a target tissue. The matrix comprises particles cross-linked to one another so that pores are defined within the matrix. The cross-linking agents used comprise biotin and avidin. The presence of pores allows the matrix to be seeded with cells for use in tissue regeneration, e.g. regeneration of the pancreas in diabetes mellitus. The matrix may be used as a scaffold for growth of new tissue or as a delivery system for therapeutic agents which teaches away from the intended use of providing biological tissue with a heparin coating disclosed in the present application.

U.S. Pat. No. 5,773,224 discloses a cell separation system utilising members of an immobilised ligand/antiligand pair, with a soluble ligand used for elution. In one embodiment immobilised heparin adsorbent is coated with biotinylated antitrombin III which is then crosslinked with avidin, thereby greatly increasing the binding affinity of antitrombin III for heparin. The resulting adsorbent effectively captures biotin-labelled target cells and allows facile elution of immunoselected cells with soluble heparin. However, this patent does not contain any teaching that would lead the skilled man to the present invention, in particular it does not teach in the direction of heparin coating of biological tissue with the purpose of down-regulating the innate immune system.

A publication by Kett, W. C. et al. (Biochim. Biophys. Acta 1620 (2003) p. 225-234) describes the interaction between avidin and glycosaminoglycans e.g. heparin which was investigated by three different methods. The results indicated that only specific polysaccharide structures tightly interact with avidin. The interaction is pH-dependent, increasing five-fold upon decreasing the pH from 7.5 to 5.5, while binding was negligible at pH 9. Kett, W. C. et al. also demonstrate the potential of fluorescent avidin derivatives as a tool for detection of heparin and heparin sulphates on surfaces by application to both heparin immobilised on polystyrene plates and heparin sulphate on cell surfaces. No teaching of methods for providing heparin coating on biological tissue is found in Kett, W. C. et al, as is disclosed in the present patent application.

In a publication by Keiser, N. et al (Nature Medicine 7 (2001) p. 123-128) a methodology to isolate, enrich and sequence tissue-derived heparin/heparin sulphate-like glucosaminoglucans (HLGAGs) that bind to specific proteins is disclosed. The generalised procedure involves immobilisation of a protein on a hydrophobic surface either directly or through a biotin-avidin system, wherein avidin is immobilised on the surface. The objective of this method is to examine how dynamic changes in cell-surface HLGAG composition and sequence influences ability of cells to alter responses to signalling molecules and elucidating polysaccharide-protein interactions. This method does not contain any teaching that would lead the skilled person to the present invention, it does not comprise heparin coating of biological tissue for the purpose of preserving the biological function of said tissue.

SUMMARY OF THE INVENTION

In view of the risk indicated above for an unwanted activation of the innate immune system after administration of exogen biological structures i.e. islets of Langerhans to the blood stream, a coating of the islets preserving their biological function without activating the innate immune system is desirable.

The present invention relates to a new method to produce a coherent and functional lining of heparin onto living cells and biological tissue with the purpose of effectively down-regulating activation of coagulation and inflammation.

Even if it has been known for some time that there is a certain affinity between heparin and avidin, it was surprisingly found that heparin, suitably as a conjugate, could bind to avidin with retained biological function and with as high affinity, or even higher, as the binding of biotin to avidin. Having discovered this, a method to modify biological tissue was elaborated based on binding of biotin to the substrate (living cells or biological tissue), subsequent binding of avidin to biotin and finally binding of the heparin conjugate to the formed layer of avidin.

The object of the present invention is thus to provide biological tissue with a heparin coating in order to preserve and even improve the biological function of said tissue.

In one aspect, the invention as defined in claim 1 relates to a method of providing biological tissue with a heparin coating comprising a first step of linking a biotin reagent to the surface of a biological tissue, a second step of linking an avidin reagent to the biotinylated biological tissue, and a third step of linking a heparin reagent to the formed layer of avidin on the biological tissue thus forming a heparin coating. The biotin reagent comprises a functional group capable of forming a chemical bond with a suitable protein residue on the tissue surface such as thiol, primary amine or carboxyl groups. The avidin reagent is linked to the biotinylated biological tissue by the strong affinity between biotin and avidin. The heparin reagent is linked to the avidin layer by the affinity between avidin and the heparin reagent. The heparin reagent should retain its capability to interact with and accelerate the inhibitory effect of antithrombin.

Suitably, the method further comprises rinsing steps after the first, the second and the third steps to remove excess amounts of reagent.

One advantage with the present invention is the achieved reproducibility obtained by the method. Other advantages are the improved biocompatibility and biological function of the biological tissue due to the coating of heparin or heparin derivatives. These features have surprisingly been found to give rise to possibilities to use the heparin coating according to present invention on any kind of implants or transplants.

BRIEF DESCRIPTION OF THE DRAWINGS

FIG. 1 illustrates the formation of a heparin coating in real time (seconds) using QCM (Quartz Crystal Microbalance).

FIG. 2 shows a heparin coated islet of Langerhans obtained by confocal microscopy.

DETAILED DESCRIPTION OF THE INVENTION

For the purpose of this application the following definitions are given. By biological tissue is meant single cells, an accumulation of cells, cluster of cells, part of an organ and whole organs. The term "layer" is defined as a molecular monolayer comprising a single continuous layer or film that is one molecule in thickness.

The term "heparin reagent" relates to heparin, heparin conjugate (a cluster of heparin molecules linked to a non-heparin molecule) or heparin derivatives or combinations thereof. It has surprisingly been found that it is possible to use a stepwise procedure to obtain a heparin coating on biological tissue with the biological functions maintained. The first step comprises linking biotin to the substrate (biological tissue). This can be accomplished by using biotin supplemented with a functional group capable of forming a chemical bond with a suitable protein residue on the tissue surface such as thiol, primary amine or carboxyl groups. A range of such biotins are commercially available. The reagent should preferably be soluble in aqueous solution and it is also preferable that the reagent has been provided with an extended chain length in order to get optimal effect. Although a number of different reagents are possible to use within the scope of the present invention, the inventors have found that a water soluble biotin reagent reactive towards primary amine groups with an extended chain length (e.g. EZ-Link™ Sulfo-NHS-LC-Biotin or EZ-Link™ Sulfo-NHS-LC-LC-Biotin or EZ-Link™ TFP-PEO-Biotin, Perbio Science, Europe) best serve the purpose of the invention. The substrate is incubated for 10-60 minutes at a temperature of 20-37° C. in a diluted solution of a biotin reagent dissolved in buffer or cell culture medium at a concentration of 0.01-1 mg/ml. A rinsing step suitably follows to remove excess reagent.

The next step is to add avidin to the biotinylated substrate. Avidin is dissolved in buffer or culture medium at a concentration of 0.01-1 mg/ml, added to the biotinylated substrate, and the biotinylated substrate is incubated for 10-60 minutes at a temperature of 20-37° C. Due to the strong affinity between biotin and avidin, the substrate surface will bind a sufficient amount of avidin. A rinsing step suitably follows to remove the excess of avidin. The third step comprises incubation of the substrate surface, now provided with a coating of avidin, in a dilute solution of heparin, preferably in the form of a macromolecular conjugate such as the heparin conjugate from Corline, Sweden, disclosed in EP 0658112. The heparin reagent is dissolved in a buffer or a culture medium at a concentration of 0.01-1 mg/ml. Incubation is performed at a temperature of 20-37° C. for 10-60 minutes. A rinsing step suitably follows to remove excess of reagent. The reaction steps described are preferably carried out at a physiological pH although it is possible to use a pH in the range of pH 5-8. Recording of the formation of heparin coating in real time may be performed by using QCM (Quartz Crystal Microbalance). With the use of the QCM instrument it is possible to follow in real time the adsorption or binding of organic molecules to specific substrate surfaces by continuously measuring the change in frequency from a crystal that oscillates at a defined frequency. The change in frequency is proportional to the change of mass.

The surface is composed of a thin layer of gold. In the first step, human albumin was adsorbed onto the gold surface in order to mimic a protein layer on a biological surface. In the next step, EZ-Link™ NHS-LC-Biotin was coupled to the layer of albumin. Due to the small size of the biotin molecule, the binding did not differentiate from the baseline curve of the QCM recording (see FIG. 1). As is shown in FIG. 1, there was a rapid and distinct change in frequency when avidin was added indicating strong binding of avidin to the biotinylated albumin. When heparin conjugate was added there was a similar rapid and distinct change in frequency. The presence of surface attached heparin with retained capability to interact with antithrombin was confirmed by adding antithrombin wherein a rapid and distinct change in frequency was recorded.

EXAMPLES

Example 1

Demonstration of the Effect by Avidin in the Formation of Heparin Coating

The following example was designed to illustrate the importance of including avidin in the coating protocol. An artificial surface, illustrated by PVC tubings, was coated with albumin to mimic a biological substrate.

PVC tubings were coated with albumin by passive adsorption by circulating a saline solution containing 2% albumin for 30 minutes at room temperature. Four groups of tubings were then incubated with three different concentrations of SPDP (N-succinimidyl 3-(2-pyridyldithio)propionate, Perbio Europe). The SPDP bound to the surface was reduced by incubation with an aqueous solution containing DTT (dithiotrietol) in order to convert the surface bound SPDP to free sulfhydryl groups. The relative occurrence of free sulfphydryl groups was measured by recording the change in absorbance at 340 nm. According to Table 1, a proportional increase of free sulfhydryl groups with increasing concentration of SPDP could be verified. In the next step biotin having a thiol-reactive end group (EZ-Link™ PEO-Iodoacetyl Biotin, Perbio Europe) was used to link biotin to the available thiol groups. Following this step, the biotinylated surfaces were exposed to a saline solution containing avidin (1 μg/ml) for 30 minutes at room temperature. Finally, the surfaces coated with avidin were exposed to a saline solution containing the heparin conjugate from Corline, Sweden, (0.1 mg/ml) for 30 minutes at room temperature.

Binding of HRP (horse radish peroxidase)-labelled streptavidin confirmed a proportional binding of biotin with increasing surface concentration of free sulfhydryl groups. The binding of heparin conjugate to the layer of avidin increased four to eight times compared with the layer of biotin without avidin and turned out to be relatively insensitive to the degree of biotin binding.

TABLE 1

Step-wise data on heparin coating of a protein coated substrate with varying surface concentrations of free sulfhydryl groups.

|  | SPDP 6 mg/ml | SPDP 0.6 mg/ml | SPDP 0.06 mg/ml |
|---|---|---|---|
| Relative occurrence of free thiol groups | 0.37 | 0.05 | 0.03 |
| Relative occurrence of surface bound biotin | 0.61 | 0.49 | 0.34 |
| Relative heparin surface conc. without avidin | 0.30 | 0.24 | 0.16 |
| Relative heparin surface conc. with avidin | 1.37 | 1.16 | 1.12 |

Example 2

Investigation of the Heparin Coating on Islets of Langerhans Using Confocal Microscopy Human islets of Langerhans were isolated according to standard procedure and kept in culture medium. A portion of islets was first incubated with biotin (EZ Link™ Sulfo-NHS-LC-Biotin, Perbio, 1 mg/ml) for 60 minutes at room temperature and then rinsed with three volumes of fresh medium. The islets were then incubated in avidin (1 mg/ml) for 30 minutes at room temperature and then again rinsed with three volumes of medium. The last incubation was performed with the heparin conjugate from Corline, Sweden, (1 mg/ml) for 60 minutes at room temperature and a final rinsing with three volumes of medium. After staining with fluorescently labelled antithrombin the heparin modified islets were compared with non-modified islets using a confocal microscope. A coherent layer of fluorescently labelled antithrombin was observed on the heparin-modified islets, as shown in FIG. 2.

Example 3

Effect on IBMIR (Instant Blood Mediated Inflammatory Response) by Heparin Modified and Non-Modified Human Islets of Langerhans Human islets of Langerhans were isolated according to standard procedure and kept in culture medium and modified with the heparin conjugate from Corline, Sweden, as previously described in Example 2 using three different types of biotin reagents (EZ-Link™ Sulfo-NHS-LC-Biotin or EZ-Link™ Sulfo-NHS-LC-LC-Biotin or EZ-Link™ TFP-PEO-Biotin). The heparin modified islets were compared with non-modified islets using the Chandler loop model, described elsewhere (Diabetes, 48, 1907-1914, 1999). Briefly, human blood without anticoagulant but supplemented with non-modified or heparin modified islets was rocked in heparin coated tubing loops at 37° C. for up to one hour. The non-modified islets provoked macroscopic clotting and the platelet count was reduced to less than five percent of the baseline level according to the Chandler loop model. There was no macroscopic clotting with heparin modified islets irrespective of biotin reagent used and the platelet count and the generation of thrombin-antithrombin complex (TAT) used as parameters to measure the degree of IBMIR were significantly improved.

Example 4

Effect on IBMIR by Heparin Modified and Non-Modified Pig Islets of Langerhans

Adult pig islets were isolated according to standard procedure and kept in culture medium and modified with the heparin conjugate from Corline, Sweden, as previously described in Example 3.

The heparin modified pig islets were compared with non-modified pig islets using the Chandler loop model as described in Example 3. The results were consistent with the results obtained in Example 3.

Example 5

Heparin Coating of Blood Vessels

Human blood vessels were dissected from a donated pancreas and kept in saline. The blood vessels were connected to small lumen tubings to facilitate perfusion of the vessels. They were first incubated with biotin (EZ Link™ Sulfo-NHS-LC-Biotin, 1 mg/ml) for 30 minutes at room temperature and then rinsed with three volumes of saline. The vessels were then incubated with avidin (1 mg/ml) for 60 minutes at room temperature and then again rinsed with three volumes of saline. The last incubation was with the heparin conjugate from Corline, Sweden, (0.1 mg/ml) for 60 minutes at room temperature and a final rinsing with three volumes of saline. Staining with toluidine blue and examination by confocal microscopy confirmed the presence of heparin on the blood vessel luminal surface.

The invention claimed is:

1. An in vitro method of providing biological tissue with a heparin coating comprising the following steps;
 (a) linking a biotin reagent to the biological tissue,
 (b) linking an avidin reagent to the biotinylated biological tissue to form a layer of avidin thereon, and
 (c) linking a heparin reagent to the formed layer of avidin on the biological tissue thus forming a heparin coating on said tissue.

2. The method according to claim 1, wherein the biotin reagent comprises a functional group capable of forming a chemical bond with a suitable protein residue on the biological tissue.

3. The method according to claim 1 or 2, wherein the heparin reagent has a capability to interact with and accelerate the inhibitory effect of antithrombin.

4. The method according to claim 1, wherein the linking of a reagent selected from the group consisting of biotin, avidin and heparin is performed at a temperature of 20-37° C.

5. The method according to claim 1, wherein the biotin reagent concentration used in the biotinylating step is in the range of 0.01-1 mg/ml.

6. The method according to claim 1, wherein the avidin reagent concentration used in the avidin linking step is in the range of 0.01-1 mg/ml.

7. The method according to claim 1, wherein the heparin reagent concentration used in the heparin linking step is in the range of 0.01-1 mg/ml.

8. The method according to claim 1, wherein a rinsing step is performed after one or more of step a), b), and c) to remove excess of reagent.

9. A heparin coating on biological tissue comprising a biotin layer, an avidin layer and a heparin layer, wherein the biotin layer comprises a biotin reagent covalently linked to the surface of the biological tissue, the avidin layer comprises an avidin reagent linked to the biotin layer by affinity, and the heparin layer comprises a heparin reagent linked to the avidin layer by affinity.

10. A biological tissue coated with heparin or a heparin reagent, wherein the heparin is linked to the tissue surface via biotin and avidin according to the steps of claim 1.

11. An implant coated with heparin or a heparin reagent, wherein the heparin is linked to the surface of the implant via biotin and avidin according to the steps of claim 1.

12. The method according to claim 2, wherein the functional group capable of forming a chemical bond with a suitable protein residue is selected from the group consisting of thiol, primary amine and carboxyl groups.

13. The method of claim 1, wherein the linking steps are carried out at a physiological pH.

14. The method of claim 1, wherein the linking steps are carried out in a pH range of 5-8.

* * * * *